(12) United States Patent
Haug

(10) Patent No.: US 8,680,054 B2
(45) Date of Patent: Mar. 25, 2014

(54) SUSPENSION TYPE TOPICAL FORMULATIONS COMPRISING CYCLIC DEPSIPEPTIDE

(75) Inventor: Claire Haug, Saint-Louis (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/445,202

(22) Filed: Apr. 12, 2012

(65) Prior Publication Data

US 2012/0270796 A1    Oct. 25, 2012

Related U.S. Application Data

(60) Provisional application No. 61/477,297, filed on Apr. 20, 2011.

(51) Int. Cl.
*A61K 38/00* (2006.01)
*A61P 17/00* (2006.01)
*A61P 29/00* (2006.01)

(52) U.S. Cl.
USPC .................................. 514/18.7; 514/18.6

(58) Field of Classification Search
None
See application file for complete search history.

(56) References Cited

U.S. PATENT DOCUMENTS

| | | | |
|---|---|---|---|
| 2009/0036487 A1* | 2/2009 | Field et al. | 514/319 |
| 2011/0112121 A1* | 5/2011 | Berghausen et al. | 514/269 |
| 2012/0064013 A1 | 3/2012 | Marcos et al. | |
| 2012/0064136 A1 | 3/2012 | Baker, Jr. et al. | |
| 2012/0328701 A1 | 12/2012 | Edelson et al. | |
| 2012/0328702 A1 | 12/2012 | Edelson et al. | |

FOREIGN PATENT DOCUMENTS

| | | | |
|---|---|---|---|
| DE | 102007052391 A1 * | 5/2009 | |
| WO | 9534558 A1 | 12/1995 | |
| WO | 2004108139 A2 | 12/2004 | |
| WO | 2005075667 A1 | 8/2005 | |
| WO | 2009024527 A1 | 2/2009 | |
| WO | 2009024528 | 2/2009 | |
| WO | WO 2009024527 A1 * | 2/2009 | |
| WO | 2011003858 A2 | 1/2011 | |

OTHER PUBLICATIONS

Pena et al "Structural Rheology of a Model Ointment" Pharm Res 6:875-881. Published Jun. 1994.*
Lautenschlager H "Active agents—the effective skin care: lipids, the basic elements" Kosmetische Praxis 6:6-8. Published 2003.*
Benson and Namjoshi "Proteins and Peptides: Strategies for Delivery to and Across the Skin" J Pharmaceutical Sci 97:3591-3610. Published online Jan. 15, 2008.*
Hiemstra, P.S., "Novel roles of protease inhibitors in infection and inflammation," Biochemical Society Transactions 30 (2):116-120 (2002).
Kunze et al., "Chondramides A-D, New Antifungal and Cytostatic Depsipeptides from Chondromyces crocatus (Myxobacteria) Production, Physico-chemical and Biological Properties," The Journal of Antibiotics 48(11)1262-1266 (Nov. 1995).
Hachem et al.; "Serine Protease Activity and Residual LEKTI Expression Determine Phenotype in Netherton Syndrome"; Journal of Investigative Dermatology; 126:1609-1621 (2006).
Hansson et al.; "Epidermal Overexpression of Stratum Corneum Chymotryptic Enzyme in Mice: A Model for Chronic Itchy Dermatitis"; J. Invest. Dermatol.; 118(3):444-449 (2002).
Vasilopoulos et al.; "Genetic Association Between an AACC Insertion in the 3'UTR of the Stratum Corneum Chymotryptic Enzyme Gene and Atopic Dermatitis"; J. Invest. Dermatol.; 123:62-66 (2004).
Harada et al., "Co-production of Microcystins and Aeruginopeptins by Natural Cyanobacterial Bloom," Environ Toxicol 16(4):298-305 (2001).
von Elert et al., "Cyanopeptolin 954, a Chlorine-Containing Chymotrypsin Inhibitor of Microcystic aeruginosa NIVA Cya 43," J. Nat. Prod. 68(9):1324-1327 (2005).
Itou et al., "Oscillapeptins A to F, Serine Protease Inhibitors from the Three Strains of Oscillatoria agardhii," Tetrahedron 55(22):6871-6882 (1999).
Namikoshi et al., "Bioactive compounds produced by cyanobacteria," J Ind Microbiol 17(5-6):373-384 (1996).
McDonough et al., "New Structural Insights into the Inhibition of Serine Proteases by Syclic Peptides from Bacteria," Chem & Biol. 10(10):898-900 (Oct. 2003).

(Continued)

*Primary Examiner* — Cecilia J Tsang
*Assistant Examiner* — Zachary J Miknis
(74) *Attorney, Agent, or Firm* — Sophie Binet Cross

(57) ABSTRACT

The invention relates to novel topical pharmaceutical compositions in which the active agent is a cyclic depsipeptide of formula (II)

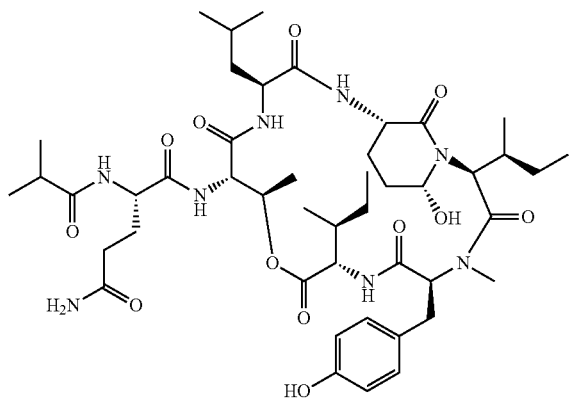

and to methods for manufacturing such compositions.

14 Claims, No Drawings

(56) References Cited

OTHER PUBLICATIONS

Franzke et al., "Antileukoprotease Inhibits Stratum Corneum Chymotryptic Enzyme," J Biol Chem 271(36):21886-21890 (Sep. 6, 1996).

Grach et al., "Protease inhibitors from a Slovenian Lake Bled toxic waterbloom of the cyanobacterium *Planktothrix rubescens*," Tetrahedron 59(42):8329-8336 (2003).

Matern et al., "Binding Structure of Elastase Inhibitor Scyptolin A," Chemistry & Biology 10(10):997-1001 (2003).

Nakanishi et al., "Structure of Porcine Pancreatic Elastase Complexed with FR901277, a Novel Macrocyclic Inhibitor of Elastases, at 1.6A Resolution" Biopolymers 53(5):434-445 (2000).

Banker R et al., "Inhibitors of Serine Proteases from a Waterbloom of the Cyanobacterium Microcystis sp," Tetrahedron 55(35):10835-10844 (Aug. 27, 1999).

Bonjouklian R et al., "A90720A, A Serine Protease Inhibitor Isolated From a Terrestrial Blue-Green Alga Microchaete loktakensis," Tetrahedron 52(2):395-404 (Jan. 8, 1996).

Reshef V et al., "Protease inhibitors from a water bloom of the cyanobacterium Microcystis aeruginosa," Tetrahedron 57(14):2885-2894 (Apr. 2, 2001).

Fairlie D P et al., "Conformational Selection of Inhibitors and Substrates by Proteolytic Enzymes: Implications for Drug Design and Polypeptide Processing," J. Med. Chem. 43(7):1271-1281 (2000).

Matthew Susan et al., "Lyngbyastatin 4, a dolastatin 13 analogue with elastase and chymotrypsin inhibitory activity from the marine cyanobacterium *Lyngbya confervoides*," J. Nat. Prod. 70(1):124-127 (Jan. 2007).

Matsuda H., "Structures of serine protease inhibitors from freshwater blue-green algae," Tennen Yuki Kagobutsu Toronkai Koen Yoshishu 35:654-661 (1993).

Radau G., "Serine proteases inhibiting cyanopeptides," Pharmazie 55(8):555-560 (Aug. 2000).

Egelrud T., "Purification and preliminary Characterization of Stratum Corneum Chymotryptic Enzyme: A Proteinase that may be involved in desquamation," J. Invest. Dermatol.101(2):200-204 (1993).

Bell and Meinardi, "The 500 Dalton rule for the skin penetration of chemical compounds and drugs," Exp Dermatol 9:165-169 (2000).

\* cited by examiner

SUSPENSION TYPE TOPICAL FORMULATIONS COMPRISING CYCLIC DEPSIPEPTIDE

This application claims benefit under 35 U.S.C. §119(e) of U.S. Provisional Application No. 61/477,297, filed Apr. 20, 2011; the contents of which is incorporated herein by reference in their entirety.

FIELD OF THE INVENTION

The present invention relates to novel topical pharmaceutical compositions in which the active agent is a cyclic depsipeptide of formula (II)

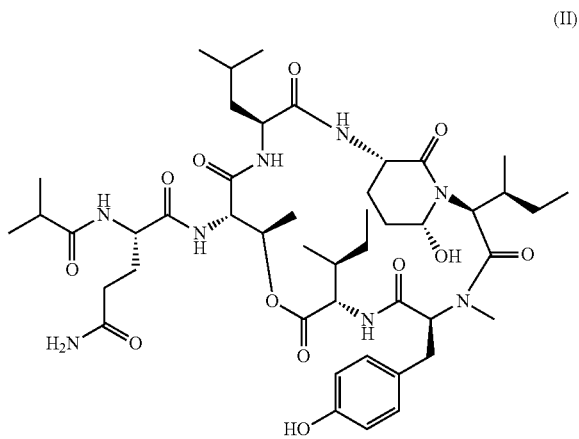 [SMILES: CC[C@H](C)[C@@H]1NC(=O)[C@H](Cc2ccc(O)cc2)N(C)C(=O)[C@H]([C@@H](C)CC)N2C(=O)[C@H](CC[C@H]2O)NC(=O)[C@H](CC(C)C)NC(=O)[C@@H](NC(=O)[C@H](CCC(N)=O)NC(=O)C(C)C)[C@@H](C)OC1=O]

(II)

and to methods for manufacturing such compositions.

BACKGROUND OF THE INVENTION

The cyclic depsipeptide of formula (II) is useful for the treatment and prevention of inflammatory and/or hyperproliferative and pruritic skin diseases such as atopic dermatitis, psoriasis, pustular psoriasis, rosacea, keloids, hypertrophic scars, acne, Netherton's syndrome or other pruritic dermatoses such as prurigo nodularis, unspecified itch of the elderly as well as other diseases with epithelial barrier dysfunction such as aged skin.

The compound of formula (II) is described in international patent application WO2009024527.

It is desirable to identify compositions, and uses of these compositions that may improve efficiency, bioavailability, stability and/or acceptance by the patient.

These objectives are achieved by providing a composition as described herein, by providing the composition for use in diseases, particular for the treatment of dermatological diseases, as described herein and by providing a process to produce the composition as described herein.

Further aspects of the invention are disclosed in the specification and independent claims, preferred embodiments are disclosed in the specification and the dependent claims.

DETAILED DESCRIPTION OF THE INVENTION

The compound of formula (II) presents highly specific difficulties in relation to topical administration and topical galenic compositions, in particular, including particular stability problems.

The compound of formula (II) shows only moderate solubility in water and aqueous buffers and low solubility in lipophilic excipients. In polar organic solvents, good solubility is observed. The compound of formula (II) has a tendency to degradeation in a hydrophilic environment, such as water and polar organic solvents/co-solvents, and is subject to hydrolysis in the presence of water.

For the treatment and prevention of diseases mentioned above, a specific penetration and permeation profile is of advantage in order to achieve high concentration of the cyclic depsipeptide of formula (II) in the skin, while limiting permeation through the skin and thus lowering systemic exposure. These special requirements necessitate the development of a non-conventional dosage form.

In accordance with the present invention it has been found that stable pharmaceutical compositions comprising cyclic depsipeptide of formula (II) having suitable penetration and permeation profiles are obtained. Consequently, the risk of occurrence of potential undesirable side-effects and/or active agent decay upon storage is diminished and overall cost of therapy may be reduced.

Terms used in the specification have the following meanings:

"Active agent" as used herein means a cyclic depsipeptide of formula (II). "Active agent" is also intended to represent amorphous and crystalline forms such as polymorphs. "Active agent" is also intended to represent a solvate thereof, a pharmaceutical acceptable salt thereof and its mixtures. "Active agent" is also intended to represent material exhibiting specific solid state properties such as specific crystal forms and/or milled forms of the "Active agent", e.g. in micronized form.

"Solvate" as used herein means a crystal form of a compound which additionally contains one or more types of solvent molecules, e.g. ethly acetate, acetonitrile, water, isopropylacetate, in a stoichiometrically defined amount. Preferably, solvates contain one type of solvent molecule in the crystal lattice.

As used herein, the term "pharmaceutically acceptable salts" refers to the nontoxic acid or alkaline earth metal salts of the active agent. These salts can be prepared in situ during the final isolation and purification of the compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydro-chloride, hydrobromide, hydroiodide, 2-hydroxyethanesulfonate, lactate, maleate, methane-sulfonate, nicotinate, 2-naphth-alenesulfonate, oxalate, pamoate, pectinate, persulfate, 3-phenylproionate, picrate, pivalate, propionate, succinate, sulfate, tartrate, thiocyanate, p-toluene-sulfonate, and undecanoate. Also, basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained. Basic addition salts can be prepared in situ during the final isolation and purification of the compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like and basic amino acids such as arginine, lysine and ornithine.

"Topical pharmaceutical composition" as used herein is known in the field (e.g. see European Pharmacopoeia, 6.3, 01/2009, 0132) and in the context of the present invention particularly refers to a composition of the suspension type. Such compositions comprise i) the active agent and ii) a matrix. The matrix (also referred to as "base") contains pharmaceutically acceptable excipients and is adapted to a topical application. Further, compositions of the invention may be formulated as semi-solid including gels, patch, foam, tincture, solution, (lip) stick, or spray; each of them in the suspension type. Consequently, viscosities of the compositions of the invention may vary over a broad range; typically they are semi-solid or liquid, preferably semi-solid. Compositions of the suspension type are characterized in that the active agent is suspended in the matrix; preferably in the form of a "hydrophobic ointment".

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context Throughout this specification and in the claims that follow, unless the context requires otherwise, the word "comprise", or variations such as "comprises" or "comprising" as well as the word "contain", or variations such as "contains" or "containing", will be understood to imply the inclusion of a stated integer or step or group of integers or steps but not the exclusion of any other integer or step or group of integers or steps.

It is further understood that the various embodiments, preferences and ranges of this invention, as provided/disclosed in the specification and claims may be combined with other specified features to provide further embodiments.

In a first aspect, the present invention provides a topical pharmaceutical composition comprising a cyclic depsipeptide of formula (II), a hydrophobic matrix and a consistency agent. It is typically a suspension type composition.

The active agent has a tendency to degrade in hydrophilic environment such as water and polar organic solvents/co-solvents and is subject to hydrolysis in the presence of water.

It was found that topical pharmaceutical compositions comprising a cyclic depsipeptide of formula (II), a hydrophobic matrix and a consistency agent, allow the active agent to be formulated into stable compositions and allow for suitable penetration and permeation profile; especially in view of the fact that the active agent is suspended in the matrix and thus only a small fraction of molecules is dissolved and available for penetration. By the use of a consistency agent it is possible to increase the level of the active agent to a pharmaceutically beneficial level in the skin without skin irritation. However, permeation of the active agent through the skin was very low, resulting in no systemic exposure or very low systemic exposure, thus minimizing the risk of side effects. Further, these compositions show good physical and chemical stability. This aspect of the invention shall be explained in further detail below:

The active agent may be obtained according to the methods described in WO2009024527. Particularly suitable for the inventive compositions are active agents of the invention in micronized form (x90<20 micrometer). The amount of active agent in the inventive composition may vary over a broad range, it is typically provided in an effective amount. An effective amount refers to an amount of the active agent which, when administered to a mammal (preferably a human), is sufficient to effect a treatment as defined below. Suitable amounts for the active agent may be determined by the skilled person in routine experiments; typically they are in the range between 0.1-5 wt. %, preferably 0.5-2.0 wt. %, such as 0.5, 0.8 or 1.0 wt. %.

Hydrophobic matrix: According to this aspect of the invention, the matrix contains paraffines (hard, liquid, light liquid), vegetable oils, animal fats, synthetic glycerides, waxes, perflourcarbons, semiperflourcarbones and/or liquid polysiloxanes. Typically, the hydrophobic matrix can absorb only small amounts of water. Preferably, the hydrophobic matrix contains one or more types of hydrocarbons; preferably at least two types of hydrocarbons. It was found that such matrix disperses a high amount of active agent and produces a stable composition. Suitable hydrocarbons are known in the field and may be selected by a skilled person to be compatible with the final pharmaceutical composition. Suitable hydrocarbons include solid and liquid hydrocarbons which may be linear and/or branched. Such hydrocarbons are known excipients for pharmaceutical compositions and are commercially available (e.g. as mixtures of individual components). Suitable hydrocarbons include "mineral oil", "petrolatum", "microcrystalline wax". A suitable hydrophobic matrix may contain up to 66 wt. % mineral oil, preferably 20-40 wt. % mineral oil. A suitable hydrophobic matrix may contain up to 98 wt. % petrolatum, preferably 40-60 wt. % petrolatum. A suitable hydrophobic matrix may contain up to 25 wt. % microcrystalline wax, preferably 5-20 wt. % microcrystalline wax. A suitable hydrophobic matrix may contain mineral oil and petrolatum in a ratio between 1:1 to 1:3, preferably 1:1.5 to 1:2.0. Further, a suitable hydrophobic matrix may contain mineral oil and microcrystalline wax in a ratio between 1:0.2 to 1:1, preferably 1:0.33 to 1:0.66.

Consistency agent: As used in the context of this invention, agents to modify consistency, also named consistency improver are known in the field. Appropriate compounds may be selected by a skilled person to be compatible with the final pharmaceutical composition. It is understood that one or more of such agents may be used. Particularly suitable are consistency agents selected from the group consisting of saturated fatty acids and saturated fatty acid esters. Preferred are saturated C6-C30 fatty acids, -esters; particularly preferred are C10-C20 fatty acids, -esters. Further, linear fatty acids, -esters are preferred. For esters, C1-C4 alkyl groups are preferred. Among these consistency agents, isopropyl myristate is particularly suitable. The amount of consistency agent in the inventive composition may vary over a broad range, it is typically provided in an effective amount. Suitable amounts of consistency agent may be determined by the skilled person in routine experiments; typically they are between 2.5-20 wt. %, preferably 2.5-10 wt. % of the total composition.

In one embodiment, the invention relates to a composition according to this aspect of the invention which contains no further excipients. Thus, the inventive composition only contains (i.e. consist of or essentially consists of) the active agent, one or more hydrocarbons and a consistency agent. Such compositions are considered advantageous e.g. for simple manufacturing and/or for patient populations with increased skin irritation/allergic potential towards other excipients.

In a further embodiment, the invention relates to a composition according to this aspect of the invention which contains one or more additional excipients. Such excipients are known in the field and may be readily identified by the skilled person. Suitable excipients may be selected from the group consisting of antioxidants, gelling agents, ph adjusting agents/buffers, penetration enhancers, preservatives, (co-)solvents and stabilizers. Such excipients are known in the field, commercially available and may be identified in standard textbooks, such as the Handbook of Pharmaceutical Excipients by R. C. Rowe et al. Such compositions are advantageous to specifically adapt to manufacturers or patients needs and thus improve product properties (like shelf life or patient compliance). Suitable further excipients are explained below:

Antioxidants are known in the field and may be selected by a skilled person to be compatible with the final pharmaceutical composition. It is understood that one or more antioxidants may be used. It was found that the antioxidant stabilizes the agent of the invention. Preferably, the antioxidant is selected from the group consisting of phenole derivatives (e.g. butylated hydroxytoluene (BHT), butylated hydroxyanisole (BHA)); ascorbic acid derivatives (e.g. ascorbic acid, ascorbyl palmiate), tocopherol derivatives (e. g. Vitamin E, Vitamin E TPGS), bisulfite derivatives (Na bisulfite, Na meta bisulfite) and thio urea. More preferably, is selected from the group consisting of butylated hydroxytoluene (BHT), butylated hydroxyanisole (BHA), alpha tocopherol, ascorbic acid or a mixture of thereof. Particularly preferably, the antioxidant is BHT. A suitable composition may contain up to 2 wt. % antioxidant, preferably 0.005-0.5 wt. %.

Gelling agents are known in the field and may be selected by a skilled person to be compatible with the final pharmaceutical composition. It is understood that one or more gelling agents may be used. Gelling agents are included in the compositions of this invention to adjust viscosity. Gelling agents that are suitable for lipophilic formulations, e.g. aerosil, polyethylen, and aluminum soap. A suitable composition may contain up to 10 wt. % gelling agent, preferably 0.02 to 2 wt. %.

Agents to adjust the pH or to provide a pH buffer are known in the field. Appropriate buffers may be selected by a skilled person to be compatible with the final pharmaceutical composition. It is understood that one or more of such buffers may be used. A suitable composition may contain such buffers to adjust the pH of the inventive composition in the range of 4-8, preferably 5-7, such as 6.5.

Penetration enhancers are known in the field and may be selected by a skilled person to be compatible with the final pharmaceutical composition. It is understood that one or more preservatives may be used. As used herein, the term "penetration enhancer" refers to a substance that enhances, i.e. improves, the penetration of the active agent when administered topically, (epicutanously), to the skin or mucosa, e.g. to skin. A wide range of penetration enhancers may be used. Suitable are penetration enhancers can for example be selected from the group consisting of:

alcohols such as ethanol, 2-propanol, propylene glycol, °leyl alcohol, linolenyl alcohol;
fatty acid ester such as butyl acetate, glycerol mono laureate, diethylene glycol oleate,
fatty acids such as oleic acid;
saponins
amines such as urea, N,N-diethyl-m-toluamide;
surfactants such as Brij 36T, PLURONIC® F68 block (copolymers based on ethylene oxide and propylene oxide),
others such as terpenes, dimethyl sulfoxide, 1,3-dioxacyloalkanes (SEPA), azone, diethylene glycol monoethyl ether, dimethylispropyladipate, dimethyl-isosorbid.

The amount of penetration enhancer in the inventive composition may vary over a broad range, it is typically provided in an effective amount. Higher penetration may also result in an increased permeation, e.g. increased permeation through the skin. Preferably, the delivery of the active agent to the systemic circulation is not or not significantly enhanced (no or no significant permeation). Suitable amounts of penetration enhancer may be determined by the skilled person in routine experiments; typically they are between 2.5-20 wt. %, preferably 2.5-10 wt. % of the total composition.

Preservatives are known in the field and may be selected by a skilled person to be compatible with the final pharmaceutical composition. It is understood that one or more preservatives may be used. Preservatives are included in the pharmaceutical compositions of this invention to increase shelf life. Preferably, preservatives are selected from the group of alcohols (e.g. benzyl alcohol), phenols, and parahydroxybenzoates. More preferably, preservatives are selected from parabens, alcohols, biguanides, mercuric salts, imidurea. A suitable composition may contain up to 5 wt. %, preferably 0.01 to 3 wt. %.

Co-solvents and solvents are known in the field and may be selected by a skilled person to be compatible with the final pharmaceutical composition; it denotes an excipient which dissolves the agent of the invention (partly or fully) and has a high miscibility with water. A solvent is an excipient which dissolves the agent of the invention but has a low miscibility with water. Thus, depending on the type of composition and the other excipients present, a specific compound may serve as a solvent or as a co-solvent. It is understood that one or more co-solvents/solvents may be used.

The active agent may be prepared as described in international patent application WO2009024527. They may include other solvents, for example solvents which may have been used for the purification or, as mentioned therein, in form of salts.

In accordance with the present invention the active agent may be present in an amount by weight of up to about 20% by weight of the composition of the invention, e.g. from about 0.05% by weight. The active agent is preferably present in an amount of 0.5 to 5% by weight of the composition, more preferably in an amount of 0.2 to 1% by weight of the composition.

The invention relates in a second aspect to a method for manufacturing compositions as described herein comprising the step of combining the excipients as described herein to obtain a hydrophobic matrix, combining the thus obtained matrix with the active agent.

A composition according to this invention may be prepared by processes that are known per se, but not yet applied for the present compositions where they thus form new processes. In general, the manufacture of a pharmaceutical composition utilizes standard pharmaceutical processes comprising the step of combining the active agent with a matrix, e.g. by mixing, dissolving and/or lyophilizing. Such steps may also comprise heating or cooling the materials used. As outlined above, the active agent is available according to known processes; the individual components of the matrix are either known per se or available according to known processes.

In one embodiment, the invention relates to a method of manufacturing a composition as described in the first aspect of the invention (i.e. a composition of the suspension type) comprising the steps of combining all excipients at a temperature between 30-95° C. to obtain a melt, adding the active agent, preferably at a temperature between 30-95° C., to obtain a suspension, homogenizing the obtained composition.

optionally cooling down the obtained composition.

The invention is illustrated by the following Examples.

| Abbreviations: | |
|---|---|
| ° C. | degree(s) Celsius |
| rpm | revolutions per minute |
| wt. % or % by weight. | weight percent |
| MBq | mega Becquerel |
| RH | relative humidity |

EXAMPLES

1. Pharmaceutical Compositions

An ointment, suspension type, was prepared by combining the excipients as indicated below with the compound of formula II. Specifically, all components as indicated below, except for the compound of formula II, were combined and heated to 80° C. with stirring to obtain a melt. The compound of formula II was added at this temperature and the resulting mixture was stirred until a complete wetting of the compound of formula II was obtained. The suspension was then homogenized with an ULTRA TURRAX: homogenizer (from company named IKA), at 24000 rpm for 5 min at 80° C. The obtained composition was slowly cooled down to 25° C. to obtain a composition of the suspension type.

| | ointment Var A [%] | ointment Var B [%] | ointment Var C [%] | ointment Var D [%] |
|---|---|---|---|---|
| Compound of formula II | 0.5 | 1.0 | 0.2 | 0.1 |
| White VASELINE (petrolatum) | 54 | 53.5 | 54.3 | 54.4 |
| liquid paraffin (mineral oil) | 30 | 30 | 30 | 30 |
| microcrystalline wax (hydrocarbons) | 12.5 | 12.5 | 12.5 | 12.5 |
| Isopropyl myristate | 3.0 | 3.0 | 3.0 | 3.0 |

2. Stability Tests

2a) Chemical Stability

The pharmaceutical compositions, as prepared above, were tested for chemical stability. After 5 months of storage at 5° C., room temperature and 40° C., less than 0.1% degradation product is detected. After 12 months of storage at 5° C., 25° C./65% RH and 30° C./65% RH, and after 6 month at 40° C. less than 0.1% degradation product is detected. The chemical stability of the compositions was found to be satisfying at long term conditions of 5° C. over 12 months and at accelerated conditions of 25° C./60% RH over 6 months. The chemical stability of the compositions was found to be very good.

2b) Physical Stability

The pharmaceutical compositions, as prepared above, were tested for physical stability. After 5 months of storage at 5° C., room temperature and 40° C., suitable particle size distribution was found at all storage conditions. After 12 months of storage at 5° C., 25° C./65% RH and 30° C./65% RH, and after 6 month at 40° C. suitable particle size distribution was found at all storage conditions. The physical stability of the compositions was found to be satisfying at long term conditions of 5° C. over 12 months and at accelerated conditions of 25° C./60% RH over 6 months. The physical stability of the compositions was found to be very good.

2c) Temperature Cycling Test

The pharmaceutical compositions, Var B and C, were tested in a temperature cycling test.

The samples were cycled between 40° C. and 5° C. in 24-hour intervals for one month.

Afterwards the physical characteristics of the samples were analyzed.

No changes of the visual and microscopic appearance were observed. A strong increase of the viscosity of the ointment could be observed.

2d) Freeze and Thawing Test

The pharmaceutical compositions, Var B and C, were tested in a freeze and thawing test.

The samples were stored for four complete freeze thaw cycles of −20° C. for 6 days, followed by 1 day at 25° C./60% RH. Samples were taken after 28 days and the physical characteristics of the samples were analyzed. No changes of the visual and microscopic appearance were observed and the viscosity of the ointment did not change.

2e) In-Use Test

The pharmaceutical composition, Var B was tested in an in-use test.

The sample was placed in white aluminum tubes (10 g) with internal protective lacquer, without imprint, with membrane, equipped with a white screw cap with a built-in point.

Approximately 0.1 g ointment was removed from the 10 g tube twice daily (morning and late afternoon) for 7 and 14 working days. After each removal of ointment, the tubes were tightly closed and stored at 25° C. until the next removal.

After an in-use period of 7 days and 14 days at 25°, the assay of the compound of formula (II) remained unchanged.

3. Allergic Contact Dermatitis (ACD) in Domestic Pigs:

For sensitization 500 μl of 10% 2,4-dinitrofluorobenzene (DNFB, dissolved in DMSO: acetone: olive oil [1:5:3, v/v/v]) were applied epicutaneously in divided volumes onto the inner lateral aspects and to the basis of both ears and onto both groins. One week later, cutaneous hypersensitivity reactions were elicited with 15 μl 1% DNFB at 12-16 sites on the shaved dorsolateral back. The test sites, 7 cm$^2$ in size, were arranged craniocaudally on both dorsal sides. Fifty microliter samples of formulations were applied to 2 test sites each on the right sides, 0.5 and 6 hrs after the challenge on day 8. The contralateral left sites were similarly treated with the vehicle (placebo) alone. The test sites were clinically examined 24 hrs after the challenge when inflammation peaked. The changes were scored on a scale from 0 to 4 (Table 3-1), allowing a combined maximal score of 12 per designated site.

TABLE 3-1

Scoring of clinical signs of test sites affected with ACD

| Score | Erythema/Intensity | Erythema/Extent | Induration |
|---|---|---|---|
| 0 | absent | absent | absent |
| 1 | scarcely visible | small spotted | scarcely palpable |
| 2 | mild | large spotted | mild hardening |
| 3 | pronounced | confluent | pronounced hardening |
| 4 | severe (or livid discoloring) | homogenous redness of test site | pronounced and elevated hardening of test site |

The results are summarized in Table 3-2.

TABLE 3-2

Inhibition of clinical ACD score by compound preparations

| Preparation | % inhibition compared to vehicle-treated controls | Statistical significance |
|---|---|---|
| 0.5% cream + linoleic acid* | 22 | p < 0.01 |
| 0.5% cream − linoleic acid** | 13 | ns |
| 0.5% ointment Var A | 16 | p < 0.05 |
| 1.0% ointment Var B | 38 | p < 0.001 |
| 1.0% in propylene glycol/ethanol 7/3 (v/v) | 33 | p < 0.01 |

*0.5% cream + linoleic acid - components: compound of formula II: 0.50%, glycerin anhydrous: 64.45%, Miglyol 812 (triglyceride mikett): 25.00%, Sedefos 75: 9.00%, butyl-hydroxytoluene: 0.05%, linoleic acid: 1.00%
**0.5% cream − linoleic acid - components: compound of formula II: 0.50%, glycerin anhydrous: 65.45%, Miglyol 812 (triglyceride mikett): 25.00%, Sedefos 75: 9.00%, butyl-hydroxytoluene: 0.05%

4. In vivo Skin Penetration/Permeability Study of the Suspension Type Formulation in Pigs In order to determine the flux (penetration) of the epicutaneously applied compound into the dermis under in vivo conditions, 4 cm$^2$ sized areas on the dorsolateral back of pigs were treated with compound formulations 8, 4, 2, and 1 hrs prior to dissection. Epidermis was removed from the excised skin after heat separation, and 6 mm punch samples of dermal sheets of 1 mm thickness from the de-epidermized skin were analysed for compound concentrations. This procedure enabled reliable determinations of drug levels in the dermis without the risk of contamination of the analytes with residual non-absorbed drug present on the treated skin surface or trapped in the superficial stratum corneum.

The drug levels obtained in the dermis are listed in Table 4-1.

TABLE 4-1

Drug levels in pig dermis after topical application in vivo

| | ointment Var B (1.0%) | | ointment Var A (0.5%) | |
|---|---|---|---|---|
| Time [hr] | Mean conc. (μg/g) | SEM (n) | Mean conc. (μg/g) | SEM (n) |
| 1 | 0.399 | 0.102 (8) | 0.077 | 0.025 |
| 2 | 0.496 | 0.209 (8) | 0.216 | 0.069 |
| 4 | 0.199 | 0.049 (8) | 0.284 | 0.126 |
| 8 | 0.426 | 0.177 (8) | 0.281 | 0.062 |

The concentrations reached in the skin after the application of 1% and 0.5% ointment over 1-8 hours were comparable to the levels reached in the in vitro skin penetration assay in whole skin after 48 hours. (see below).

Penetration into Stratum Corneum of Pig Skin in vivo

Lateral thighs of domestic pigs were treated topically with ointment Var B (1.0%) 2 hrs and, contralaterally 0.5 hr prior to the dissection of the treated skin samples. Excess of applied material was removed by wiping with a paper towel. D SQUAME® tapes (adhesive tape for skin sampling, 2.2 cm in diameter, CuDerm) were used to serially remove 40 serial layers of stratum corneum using and air pressure-driven plunger to obtain uniform pressure. Compound levels were analyzed and normalized to the skin area stripped.

Compound levels in the stratum corneum (sum of 40 tape strip extracts) amounted to a total of 3.6 μg/m$^2$ and 7.5 μg/cm$^2$ 0.5 and 2 hours after application of the ointment Var B (1.0%), respectively.

5. In vitro Skin Penetration/Permeation in Human Abdominal Cadaver Skin

Skin Preparation

Frozen human abdominal cadaver skin was obtained from the West Hungarian Regional Tissue Bank, Györ, Hungary (Batch No. 090620-9 (=batch 1) and 090609-8 (=batch 2), from a 69 and a 61-years old female donor, respectively. Before starting the experiment, the skin was kept at −20° C. for approximately 4 months. Thawed skin samples were dermatomized to a thickness of 500 μm with an AESCULAP dermatome (Aesculap AG, Tuttlingen, Germany), cut to fit into the diffusion area, and assembled between the donor and the receptor chambers of the diffusion Franz cells (Franz 1975).

Determination of the Skin Integrity

The integrity of skin was determined by evaluating the permeation of tritiated water ($^3H_2O$) through the skin; 400 μL of $^3H_2O$ (0.1 MBq/mL) were applied to the surface of the skin. After 30 min of equilibration, the $^3H_2O$ was removed from the skin with cotton tips; 2 mL of the receptor phase (composition of the receptor fluid described below) were sampled in order to measure the fraction of $^3H_2O$ which permeated across the skin. Radioactivity in the receptor phase was measured by liquid scintillation counting in Liquid Scintillation Systems 2500 TR (Packard Instr. Co., Meriden, Conn., USA). For quench correction an external standard method was used. Quench correction curves were established by means of sealed standards (Packard Instr.)

Determination of the in vitro Skin Permeation Through the Skin and Penetration into the Skin The skin was used as a membrane separating the donor and receptor chambers of the manual static Franz cells (volume of approximately 7.3 mL, 16 mm internal diameter). The receptor chamber was filled with the receptor fluid (0.5% aqueous solution of Brij 78 [Volpo20]) to simulate the human physiological conditions and the systemic removal of the drug from skin. The receptor fluid contained in addition 100 U/mL of a 1% penicillin/streptomycin mixture to prevent microbiological contamination.

The effective skin areas for diffusion and the volumes of receiver compartment were in the range of 1.78 to 2.14 cm$^2$ (mean 2.01 cm$^2$) and 6.98 to 7.54 mL, respectively. The temperature of the cells was kept constant using a circulating water bath at 34±1° C. Magnetic stirrer bars were constantly used during the entire experiment to ensure receptor uniformity.

Collection and Handling of the Samples

The formulations a-c (Table 5) in amounts of 243-305 mg and 0.300 mL of formulation d were applied as a single dose on the skin samples mounted on the diffusion Franz cells (corresponding to sampling time=0 h, 3-4 cells per formulation). The formulations were left on the skin for 48 h. To avoid evaporation and dryness of the formulations, the donor compartments of Franz cells were semi-occluded with parafilm (Parafilm® M) containing holes. For determination of active agent that permeated across the skin, aliquots of 200 μL of the receptor fluid were collected from the receptor compartment at 4, 7, 20, 25.5, 28, 31, 44, and 48 h after application. The volume taken from the receptor compartment was replaced every time with the same volume of fresh receptor fluid in order to keep the total receptor fluid volume constant during the entire assay period.

At the end of the treatment period (48 h post application), the residual formulation on the surface of each skin sample was carefully removed with a cotton tip applicator, and the application area was washed with a cotton containing water and gently dried with new cotton applicators. The procedure was repeated three times. The stratum corneum was then separated from the skin by 21 tape strips using a commercial adhesive tape (Scotch® 550, 3M). The first strip was discarded in order to avoid potential contamination from the formulation and the remaining 20 strips were placed into vials (strips no. 2-6, 7-11, 12-16, 17-21 pooled together). Biopsies of the treated area of the stripped skin were taken with a 1.2 cm diameter punch and weighed. Receptor fluids, tape strips, and stripped skins samples were frozen and kept at −20° C. until analysis. The concentration of the cyclic depsipeptide of formula (II) in samples was determined by a validated LC-MS/MS analysis; the lower limit of quantification was 0.5 ng/mL (receptor fluid and strips) or 5 ng/g (skin samples).

What is claimed is:

1. A topical pharmaceutical composition of suspension type comprising a cyclic depsipeptide of formula (II)

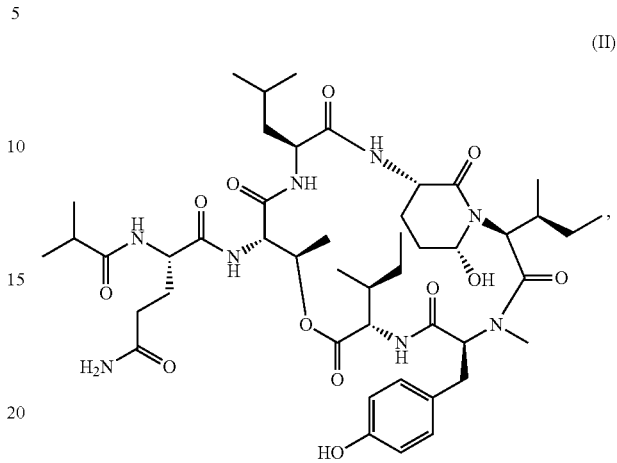

(II)

a hydrophobic matrix and isopropyl myristate as a consistency agent.

2. A pharmaceutical composition according to claim 1, in form of a hydrophobic ointment.

3. A pharmaceutical composition according to claim 1, wherein the hydrophobic matrix includes one or more compounds selected from the group consisting of paraffines, vegetable oils, animal fats, synthetic glycerides, waxes, perflourcarbons, semiperflourcarbones and liquid polysiloxanes.

4. A composition according to claim 1, wherein the hydrophobic matrix includes at least two types of hydrocarbons selected from the group consisting of mineral oil, petrolatum, and microcrystalline wax.

5. A composition according to claim 1 further comprising one or more excipients selected from the group consisting of:
   a. an antioxidant which is butylated hydroxytoluene,
   b. gelling agents selected from the group consisting of colloidal silicon dioxide, polyethylen, and aluminum soap,
   c. ph adjusting agents/buffers,
   d. penetration enhancers selected from the group consisting of ethanol, 2-propanol, propylene glycol, oleyl alcohol, linolenyl alcohol, butyl acetate, glycerol mono lau-

TABLE 5

| Formulation/cyclic depsipeptide of formula (II) | ointment Var D (0.1%) | ointment Var A (0.5%) | ointment Var B (1.0%) | 1% in propylene glycol/ethanol 7/3 (v/v) |
|---|---|---|---|---|
| Concentration in the stratum corneum: 2-21 strips (ng/cm$^2$) | 3270 [2730-3810] | 5330 ± 3730 [2090-10600] | 4920 ± 3180 [1250-6680] | 50.3 ± 62.1 [0.00-120] |
| Skin concentration after 48 h (ng/cm$^2$) | 2.17 ± 3.68 [0.187-7.69] 0.330 ± 0.013$^a$ | 11.4 ± 15.1 [1.02-33.7] 3.90 ± 0.259$^a$ | 20.8 ± 32.4 [0.479-68.5] 4.91 ± 0.749$^a$ | 185 ± 196 [1.32-391] |
| Skin concentration after 48 h (ng/g) | 48.1 ± 83.3 [5.08-173] 6.40 ± 0.144$^a$ | 204 ± 300 [16.9-652] 54.7 ± 3.36$^a$ | 370 ± 606 [9.63-1270] 70.1 ± 10.3$^a$ | 3520 ± 3620 [39.4-7260] |
| Flux [range] (ng/cm$^2$/h) | 0.825 ± 1.65 [0.00-3.30] 0.00 ± 0.00$^a$ | 0.970 ± 1.94 [0.00-3.88] 0.00 ± 0.00$^a$ | 4.63 ± 9.26 [0.00-18.5] 0.00 ± 0.00$^a$ | 25.0 ± 26.0 [0.00-51.8] |
| Lag time (h) | 0.422 NC$^a$ | 15.4 NC$^a$ | 13.2 NC$^a$ | 17.9 |

$^a$highest value (outlier) excluded, SD calculated for n > 2 reate, diethylene glycol oleate, oleic acid, saponins, urea and N,N-diethyl-m-toluamide; and
e. preservatives selected from the group consisting of parabens, alcohols, biguanides, mercuric salts, imidurea.

6. A composition according to claim 1 further comprising one or more penetration enhancer selected from the group consisting of ethanol, 2-propanol, propylene glycol, oleyl alcohol, linolenyl alcohol, butyl acetate, glycerol mono laureate, diethylene glycol oleate, oleic acid, saponins, urea and N,N-diethyl-m-toluamide.

7. A composition according to claim 1, wherein the cyclic depsipeptide of formula (II) is present in an amount between 0.1-5 wt. % of the total composition, the consistency agent is present in an amount between 2.5-20 wt. % of the total composition and the hydrophobic matrix contains up to 66 wt. % mineral oil, up to 98 wt. % petrolatum, up to 25 wt. % microcrystalline wax.

8. A pharmaceutical composition according to claim 2, wherein the hydrophobic matrix includes one or more compounds selected from the group consisting of paraffines, vegetable oils, animal fats, synthetic glycerides, waxes, perflourcarbons, semiperflourcarbones and liquid polysiloxanes.

9. A composition according to claim 2, wherein the hydrophobic matrix includes at least two types of hydrocarbons selected from the group consisting of mineral oil, petrolatum, and microcrystalline wax.

10. A composition according to claim 3, wherein the hydrophobic matrix includes at least two types of hydrocarbons selected from the group consisting of mineral oil, petrolatum, and microcrystalline wax.

11. A composition according to claim 2, wherein the cyclic depsipeptide of formula (II) is present in an amount between 0.1-5 wt. % of the total composition, the consistency agent is present in an amount between 2.5-20 wt. % of the total composition and the hydrophobic matrix contains up to 66 wt. % mineral oil, up to 98 wt. % petrolatum, up to 25 wt. % microcrystalline wax.

12. A composition according to claim 3, wherein the cyclic depsipeptide of formula (II) is present in an amount between 0.1-5 wt. % of the total composition, the consistency agent is present in an amount between 2.5-20 wt. % of the total composition and the hydrophobic matrix contains up to 66 wt. % mineral oil, up to 98 wt. % petrolatum, up to 25 wt. % microcrystalline wax.

13. A composition according to claim 4, wherein the cyclic depsipeptide of formula (II) is present in an amount between 0.1-5 wt. % of the total composition, the consistency agent is present in an amount between 2.5-20 wt. % of the total composition and the hydrophobic matrix contains up to 66 wt. % mineral oil, up to 98 wt. % petrolatum, up to 25 wt. % microcrystalline wax.

14. A composition according to claim 5, wherein the cyclic depsipeptide of formula (II) is present in an amount between 0.1-5 wt. % of the total composition, the consistency agent is present in an amount between 2.5-20 wt. % of the total composition and the hydrophobic matrix contains up to 66 wt. % mineral oil, up to 98 wt. % petrolatum, up to 25 wt. % microcrystalline wax.

* * * * *

UNITED STATES PATENT AND TRADEMARK OFFICE
CERTIFICATE OF CORRECTION

| | | |
|---|---|---|
| PATENT NO. | : 8,680,054 B2 | Page 1 of 1 |
| APPLICATION NO. | : 13/445202 | |
| DATED | : March 25, 2014 | |
| INVENTOR(S) | : Haug | |

It is certified that error appears in the above-identified patent and that said Letters Patent is hereby corrected as shown below:

In the Claims

At column 13, claim number 8, line numbers 18-22, please amend claim 8 as follow:

8. A pharmaceutical composition according to claim 2, wherein the hydrophobic matrix includes one or more compounds selected from the group consisting of parafines, Vegetable oils, animal fats, synthetic glycerides, Waxes, perfluorocarbons, semiperfluorocarbons and liquid polysiloxanes.

Signed and Sealed this
Twenty-first Day of July, 2015

Michelle K. Lee
*Director of the United States Patent and Trademark Office*